United States Patent [19]

Davitz

[11] Patent Number: 4,865,809
[45] Date of Patent: Sep. 12, 1989

[54] COPPER-FREE GOLD ALLOY COMPOSITION

[76] Inventor: Daniel Davitz, 921 Harlem, Glenview, Ill. 60025

[21] Appl. No.: 251,688

[22] Filed: Sep. 30, 1988

[51] Int. Cl.[4] ............................................. C22C 30/00
[52] U.S. Cl. .................................................... 420/580
[58] Field of Search ................................ 420/580, 505

[56] References Cited

U.S. PATENT DOCUMENTS 1,987,451  1/1935  Taylor ................................. 420/509
4,411,863  10/1983  Otsuka et al. ....................... 420/505

Primary Examiner—L. Dewayne Rutledge
Assistant Examiner—David Schumaker
Attorney, Agent, or Firm—Robert S. Beiser

[57] ABSTRACT

A gold colored, tarnish and corrosion resistant copper free allow is disclosed usable for jewelry, dental purposes and the like. The alloy consists essentially of 8 to 20 percent Gold, 22 to 26 percent Indium, 22 to 28 percent Palladium, and the balance is essentially Silver.

8 Claims, No Drawings

COPPER-FREE GOLD ALLOY COMPOSITION

BACKGROUND OF INVENTION

Gold is generally alloyed with other metals for use in jewelry and in dentistry. Such alloys require a relatively low melting point and must form a generally fluid melt with a low surface tension to permit conformance to intricate molds. When used in jewelry, gold alloys must preserve the look of gold and should be capable of being readily worked and polished. In the dental field as in the jewelry field, corrosion and tarnishing are a concern and gold alloys should not easily tarnish and corrode.

In jewelry application, color is a particularly important feature. Gold, Copper and Silver are generally used to adjust color with copper always used with the gold color jewelry alloys. In dentistry application, gold alloys are used for restorations and bridges, inlays and partial dentures. These applications must be castable and in fact replaced wrought wire in many of these appliances. In attempts of the prior art to develop a gold alloy possessing the true color of gold while maintaining its capabilities of being readily workable and polished, various non-precious metals and gold have been tried. For example, the present applicants U.S. Pat. No. 4,350,527 is directed to a gold colored alloy having 0 to 10 percent gold content with 7 to 20 percent copper, 15 to 20 percent indium and 5 to 15 percent palladium.

A number of U.S. Patents describe gold alloys for use in jewelry and dentistry, but all contain copper. U.S. Pat. No. 1,987,451 contains 25 to 65 percent gold, 2 to 25 percent palladium, 10 to 33 percent silver, 10 to 25 percent copper and 0.5 to 5 percent indium. U.S. Pat. No. 4,264,359 contains 25 percent gold, 12 to 13 percent palladium, 10 to 12 percent silver, 9 to 10 percent zinc, 0.045 to 0.65 percent boron, and the balance consisting of copper. U.S. Pat. No. 4,370,164 contains 4 to 10 percent gold, 54 to 61 percent silver, 14 to 19 percent copper, 4 to 7 percent palladium, 9 to 14 percent indium and 1 to 3 percent zinc. All of these patents include a substantial percentage of copper by weight to achieve the gold colored alloy. U.S. Pat. No. 4,038,074 discloses a nickel-chromium based alloy containing 63 to 75 nickel, 17 to 22 percent chromium, 2.5 to 5 percent molybdenum, 1 to 5 percent cobalt, 2 to 3 percent boron, 0 to 1 percent iron, and 0 to 5 percent copper, with the preferred embodiment having 0 percent copper. However, this patent is for a metal alloy which is not gold colored.

SUMMARY OF THE INVENTION

Accordingly, an object of the present invention is to provide a tarnish resistant and corrosion resistant alloy which enhances the gold color without the use of copper.

An additional object of the present invention is a metal alloy having chemical and physical properties suitable for use in jewelry and dentistry applications.

A further object of the present invention is a gold alloy having enhanced tarnish resistance by eliminating the use of copper and still having rich gold appearance.

Other objects of the present invention and advantages accruing therefrom will be apparent to one skilled in the art in the following detailed description. All percentages referred to are percent by weight based on the total weight of the material or mixture then referred to.

DETAILED DESCRIPTION OF THE PREFERRED EMBODIMENT

In accordance with the present invention a metal alloy is disclosed which is tarnish resistant and corrosion resistant and consists of the following ingredients: 22 to 26 percent indium, 18 to 28 percent palladium, 8 to 20 percent gold, the remainder consisting essentially of silver. The alloys in accordance with the subject invention are a rich gold color which approximates a higher carat alloy. In addition, tarnish resistance and corrosion resistance are greatly increased.

It may be desirable to add 0.25 to 1.5 percent Zinc to act as a scavenger. This can provide a spontaneous purifying capability of the alloy, in that the zinc can react with the oxygen or oxides.

As mentioned above, in the present alloy, only 8 to 20 percent gold is present. Despite such low gold content, the alloy exhibits a rich gold color and maintains a high tarnish resistance due to the absence of copper. It has been found that without the presence of the higher percentage of indium and lower silver, the alloy would appear white (silver color). However, it has been found that a higher percentage of indium in the presence of gold turns the alloy yellow. The higher the gold content, the less silver content is required to obtain a richer gold color. It is believed that this occurs because the palladium and silver develop a grain structure with each grain surrounded by the mixture of indium and gold. The Indium draws out and dissolves the gold into itself. The resulting alloy exhibits a rich gold appearance. An increase in tarnish resistance from the copper alloys is also obtained not only in the absence of copper, but with increase of palladium. This material acts to strongly reduce tarnishing and corrosion.

While it is noted that 22 to 26 percent of indium may be present in the present alloy it is generally preferred that 23 percent is present. In addition, while only 8 to 20 percent gold is present in the alloy of the subject invention 14 percent is preferred. Despite such low gold content, this alloy exhibits a rich gold color and maintains a very high degree of tarnish and corrosion resistant properties.

Palladium generally appears to strongly inhibit the tarnishing of this alloy as well as the absence of copper. A lower percentage of palladium and a higher percentage of silver will cause these alloys to become white with lower tarnish and corrosion resistance. Thus while 22 to 28 percent palladium may be used in furtherance of the invention, palladium concentration of approximately 26.5 percent is preferred and found optimal.

The casting temperature of the present invention described is approximately 2150 degrees F. and the melting temperature is approximately 1985 degrees F. Such temperatures are sufficiently low to permit the formation of a melt and easy casting. Ruthenium also can be added to the alloy to prevent grain growth. Boron can be added to inhibit oxidation caused from the heat of the melting.

The specific gravity of the preferred alloy is 9.35 grams/cubic centimeter plus or minus 0.5.

Preferred alloy formula:
Au. 14%
Pd. 26.5%
Ag. 36.5%
In. 23%

Because of the absence of copper the alloy becomes highly tarnish resistant in a liver sulfate atmosphere and a solution of 30% chlorine and H₂O.

While the invention has been described with reference to a preferred content and formula, it will be understood by those skilled in the art that various changes may be made and equivalents substituted for elements described herein without departing from the scope of the invention. In addition, many modifications may be made to adapt to a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A gold color, highly tarnish and corrosion resistant alloy which consists essentially of 22 to 26 percent Indium, 22 to 28 percent Palladium, 8 to 20 percent Gold, and the balance consisting essentially of Silver, and wherein said alloy is copper free.

2. The alloy of claim 1 having a casting temperature of approximately 2150 degrees.

3. The alloy of claim 1 having a casting temperature of approximately 1985 degrees.

4. The alloy of claim 1 in which said balance of silver does not exceed 39 percent.

5. A dental alloy suitable for crown, bridges, and other dental apparatus which consists essentially of a gold colored, highly tarnished resistant and corrosion resistant alloy containing approximately 14 percent Gold, approximately 23 percent Indium, approximately 26.5 percent Palladium and the balance Silver.

6. An article of jewelry made of an alloy consisting essentially of approximately 14 percent Gold, approximately 23 percent Indium, approximately 26.5 percent Palladium, and the balance is Silver.

7. An article of jewelry formed of the alloy of claim 1.

8. The alloy of claim 1 wherein said alloy has a specific gravity of 9.35 grams per cubic centimeter plus or minus 0.5.

* * * * *

UNITED STATES PATENT AND TRADEMARK OFFICE
CERTIFICATE OF CORRECTION

PATENT NO. : 4,865,809
DATED : September 12, 1989
INVENTOR(S) : Daniel Davitz

It is certified that error appears in the above-identified patent and that said Letters Patent is hereby corrected as shown below:

Abstract, line 2, "allow" should read --alloy--.

Column 4, line 5, "casting" should read --melting--.

Signed and Sealed this

Eleventh Day of September, 1990

Attest:

HARRY F. MANBECK, JR.

*Attesting Officer*   *Commissioner of Patents and Trademarks*